United States Patent [19]

Hanker et al.

[11] Patent Number: 4,619,655
[45] Date of Patent: Oct. 28, 1986

[54] PLASTER OF PARIS AS A BIORESORBABLE SCAFFOLD IN IMPLANTS FOR BONE REPAIR

[75] Inventors: Jacob S. Hanker; Bill C. Terry; Wallace W. Ambrose; Cecel R. Lupton, all of Chapel Hill, N.C.

[73] Assignee: University of North Carolina, Chapel Hill, N.C.

[21] Appl. No.: 574,168

[22] Filed: Jan. 26, 1984

[51] Int. Cl.$^4$ .............................................. C09K 3/00
[52] U.S. Cl. ......................................... 623/1; 623/16; 128/90; 128/91 R
[58] Field of Search ...................... 128/90, 91 R, 92 C; 623/16

[56] References Cited

U.S. PATENT DOCUMENTS

| | | | |
|---|---|---|---|
| 4,097,935 | 7/1978 | Jarcho | 623/16 |
| 4,195,366 | 4/1980 | Jarcho et al. | 623/16 |
| 4,439,152 | 3/1984 | Small . | |

OTHER PUBLICATIONS

Hanker, J. et al, "Revascularization During Experimental Mandibular Defect Repair", AADR Abstracts, *J. Dent. Res.*, 62, 195 (1983).
Frame, J. W., "Porous Calcium Sulphate Bihydrate as a Biodegradable Implant in Bone," *Journal of Dentistry*, 3, 177–187 (1975).
Alderman, Norman E., "Sterile Plaster of Paris as an Implant in the Infrabony Environment; A Preliminary Study," *J. Periodontol*, 40, 11–13, (1969).
Peltier, Leonard F., "The Use of Plaster of Paris to Fill Defects in Bone", *Clin. Orthop.*, 21, 1–31 (1961).
Bahn, Saul L., et al., "Plaster: A Bone Substitute," *O.S., O.M. & O.P.*, 21, No. 5, 672–681 (1966).
Calhoun, Noah R., et al., "Plaster: A Bone Substitute in the Mandible of Dogs," *J. Dent, Res.*, 44, 940–946 (1965).
Calhoun, Noah R., et al., "Plaster of Paris Implants in the Mandible of Dogs," *Quart, Nat. DA*, 21, 13–15 (1962).
Mitchell, David F., et al., "Osteogenic Potential of Calcium Hydroxide and Other Materials in Soft Tissue and Bone Wounds," *J. Dent. Res.*, 37, 1157–63 (1958).
Hogset, O. et al, "An Electrocochleographic Study of the Effect of Plaster of Paris Implanted in the Middle Ear of the Guinea Pig", Biomaterials in Otology, pp. 105–116 (1983).
Peltier, Leonard, "The Use of Plaster of Paris to Fill Large Defects in Bone," *Amer. J. of Surg.*, 97, 311–315 (1959).
Beeson, William H., "Plaster of Paris as an Alloplastic Implant in the Frontal Sinus," *Arch. Otolaryngol.*, 107, 664–669 (1981).
Coetzee, Andries S., "Regeneration of Bone in the Presence of Calcium Sulfate," *Arch Otolaryngol.*, 106, 405–409 (1980).
Radentz, William H. et al, "The Implantation of Plaster of Paris in the Aveolar Process of the Dog," *J. Periodont.*, 36, 357–364 (1965).

*Primary Examiner*—John Kight
*Assistant Examiner*—M. L. Moore
*Attorney, Agent, or Firm*—Cushman, Darby & Cushman

[57] ABSTRACT

Plaster of Paris is employed to form implants as well as a bioresorbable scaffold for implants and bone repair in animals. In bone repair, the plaster is mixed with a non-bioresorbable calcium source, such as calcium phosphate ceramic, to stimulate bone formation. Plaster may also be used as a medicament implant, encasing the active material for subsequent release to the body.

18 Claims, No Drawings

PLASTER OF PARIS AS A BIORESORBABLE SCAFFOLD IN IMPLANTS FOR BONE REPAIR

The invention was made in connection with work sponsored by the U.S. Navy Medical Research & Development Command under ONR Contract N00014-82-K-0305.

BACKGROUND AND SUMMARY OF THE INVENTION

The present invention relates to certain novel bone implants and their use for bone repair or reconstruction.

Broadly described, the implants of the invention comprise a mixture of Plaster of Paris (PP) or equivalent forms of calcium sulfate hemihydrate, hereinafter referred to for convenience as "plaster", and calcium phosphate ceramic particles, the plaster functioning as a malleable, biodegradable "scaffold" or binder to hold the ceramic particles together.

According to one embodiment of the present invention, it is necessary for successful bone implants to use both the plaster and a relatively non-resorbable calcium containing material, such as calcium phosphate ceramic. The plaster, as noted, serves as a scaffold for the ceramic, contains the mixture in a desired physical form to fill a bony cavity or defect, and augments form or contour. The plaster also provides a source of calcium in the area of the implant and stimulates revascularization and bone formation.

Conventional pharmaceutical grade Plaster of Paris or like calcium sulfate hemihydrate may be used for present purposes. Similarly, any available calcium phosphate ceramic particles may be employed. Preferably, however, these are composed of hydroxylapatite (HA), tricalcium phosphate (TCP—e.g. Augmen) or mixtures thereof. Hydroxylapatite particles are available, for example, as Calcitite 20-40 or Durapatite 18-40. Such particles are obtained by sintering or firing the mineral hydroxylapatite $Ca_{10}(PO_4)_6(OH)_2$ at about 1200° C.

DETAILED DESCRIPTION OF THE INVENTION

The present invention thus provides an animal (preferably human) implant composed of a binder lattice or scaffold of Plaster of Paris and a non-bioresorbable calcium material such as calcium phosphate ceramic particles.

According to a further embodiment, the implant may contain an active medicament bound within the plaster for administration to a patient in need of an effective amount of the medicament.

The implants of the present invention may serve to facilitate the replacement of fibrous tissue and/or heal fracture areas within a patient when placed at an appropriate locus within the patient.

Tests show that when alloplasts composed of 50/50 mixtures of HA/PP were implanted into experimentally-created defects in rat mandible, the PP was completely resorbed within a few weeks and replaced by connective tissue. The HA was not resorbed and some particles were eventually completely surrounded by bone. Thus, the PP appears to act as a scaffold for the incorporation of HA into bone. Human tissue specimens from patients who had previously undergone ridge augmentation with HA were obtained when vestibuloplasty was required. These specimens appeared to consist primarily of connective tissue and HA. Study of these samples with the PATS reaction and modified Papanicolaou trichrome stain indicate that the tissue response of humans to HA is similar to that of rats with respect to capsule formation. These findings indicate that HA/PP implants, with metal alloy or surgical mesh reinforcement when required, are useful for repair of experimental bone discontinuities and extensive bone loss in experimental animals.

Particle size for the ceramic can be widely varied. Usually, however, this will be in the range of about 20 to 60 mesh.

The ratio of non-resorbable calcium material to plaster can also be varied. The important consideration is to use enough plaster to effectively bind the non-resorbable, e.g., ceramic, particles together. Usually the ratio of ceramic to plaster, on a weight basis, will be in the range of 0.5–6, and preferably about 1, parts ceramic per part of plaster.

Other materials may also be included in the implant compositions of the invention in addition to the plaster and non-resorbable calcium material, i.e., calcium phosphate ceramic particles. Thus, for example, particles of materials such as alumina, autologous freeze-dried bone or demineralized freeze-dried bone can be mixed with the plaster and calcium phosphate ceramic. Whatever the specific makeup of the implant composition, however, the plaster functions as a biodegradable scaffold or binder for the implant. Tests show that the plaster is resorbed within a few weeks of implantation, being replaced by fibrovascular connective tissues, capsules, and new bone which hold the nonresorbable ceramic particles together and aid their incorporation into host bone.

It will be appreciated that implants according to the invention may be modified to include reinforcing or support materials. For example, the implants may include stainless steel, titanium, bars or fixation plates where rigid internal fixation is required. Alternatively, the implants can be supported by materials such as metallic or plastic surgical mesh. Such implants can be screwed into, wired to, or glued to intact bone to achieve the desired stabilization.

The implant composition of the invention may be preformed into the desired shape or shapes or it may be made up as a dry mix which can be moistened with water just prior to use to provide a fluid or semisolid, injectable formulation which can be injected into the appropriate body space as required for bone reconstruction. For example, a fluid plaster/calcium phosphate ceramic (HA) mixture may be injected into a subperiosteal tunnel for mandibular ridge augmentation to achieve greater ridge height than can be attained by injection of hydroxylapatite (HA) in saline. Preforms according to the invention can be used in reconstructive orthopedic, craniofacial, or maxillofacial surgery for massive bone loss due to resorption, e.g. due to tumors or tooth loss or in traumatic injury such as extensively comminuted fractures. In such a case, the implants can be formed in the operating room for repair of pathologic fractures (as seen in bone weakened by tumors, cysts, osteomyelitis, osteoporosis) or for skull fractures.

Unique and advantageous features of the present invention include the following:

(1) The implants are readily sterilized and can be easily formed or molded in the operating room (or chairside) as required. For ridge augmentation, a hydroxylapatite/plaster mixture can be injected into a subperiosteal tunnel by syringe. If preformed, the implants can readily be contoured as required at the time of implantation;

(2) The mixture of plaster and nonresorbable calcium material act as local sources of calcium which apparently stimulate osteogenesis;

(3) The plaster is totally resorbed within a few weeks, being replaced initially by fibrous connective tissue. The calcium phosphate is resorbed at a much slower rate and acts as a source of calcium over a longer period of time. The nonresorbed ceramic implant particles and fibrous connective tissue in contact with bone or periosteum become incorporated into new bone;

(4) The rate of resorption of the plaster can be adjusted by mixing with other biodegradable substances such as butyl cyanoacrylate adhesive. The density of the plaster can also be varied to adjust the resorption rate;

(5) All of the materials contemplated for use in the implants of the invention are inert and easy to process. The individual components of the implant are approved, or derived from materials approved, for internal use and they are readily miscible with each other.

The invention is illustrated by the following examples:

EXAMPLE 1

Callus formation in fracture healing is initiated by cell proliferation and capillary sprouting from the periosteum, bone marrow and surrounding connective tissue. The purpose of this example was to compare capillary sprout cells in a healing versus a nonhealing mandibular defect in rats. Full-thickness defects were created in rats by drilling bilaterally exposed mandibular rami with a 4 mm rotary drill (Kaban and Glowacki, J. Dent. Res. 60, 1356, 1981). Healing of defects was stimulated on one side by filling with a 4:1 moistened mixture of hydroxylapatite (Calcitite 40/60) and Plaster of Paris. The opposite side was left as a nonhealing control defect. After 2 weeks, the rats were sacrificed. Specimens of both defects were fixed, decalcified, sectioned and stained to demonstrate the microvasculature basement membranes. In evaluating the resorptive nature of Plaster of Paris, and its ability to stimulate the growth of fibrovascular tissue, a new and effective staining technique (referred to herein as the PATS reaction) was used.

Sectional specimens were treated with 1% periodic acid for thirty minutes and then rinsed with distilled water. The specimens were then treated for 15 minutes with a 20% acetic acid solution having 0.2% thiocarbohydrazide dissolved therein. The specimens were again rinsed in distilled water and immersed in an ammoniacal aqueous 1% silver methenamine solution under a UV lamp for 15 minutes. The specimens were then rinsed in distilled water, allowed to stand in glycerine overnight and cover slipped.

There was intense proliferation of capillary sprouts, endothelial cells, fibroblasts, and connective tissue fibers in the filled healing defect only. The basement membranes of the sprouts and endothelium were stained prominently by the PATS reaction in marrow, connective tissue and periosteum adjacent to the bone trabeculae. The large number of reticular fibers due to granulation were stained because of their argyrophilia, but were not as prominent as capillary basement membranes. The nearby muscle microvasculature in the healing defect appeared to have undergone more extensive sprouting.

EXAMPLE 2

This example illustrates the advantage of Plaster of Paris (PP) as a binder instead of other possible biodegradable binding agents namely, bovine serum albumin and collagen, when used with hydroxylapatite (HA) ceramic particles for repair of experimental bony defects in rats. The results (Table 1) show that plaster (PP) was the most useful and versatile material for this purpose. The PP was completely resorbed within a few weeks and replaced by connective tissue. The HA was not resorbed and some particles were eventually completely surrounded by bone. When PP was used as the binder for the HA particles, ossification of the HA (Calcitite or Durapatite) particles was much more pronounced than when collagen or bovine serum albumin (BSA) were employed (Table 1).

In similar experiments in rabbits and monkeys, even when the composite ceramic alloplasts were reinforced by stainless steel, titanium or Vitallium wire, bar or mesh, no swelling, inflammation or infection were observed.

A non-immunologic, reparative foreign-body granuloma appeared to aid incorporation of the implants and prevent their rejection by the host.

In monkeys, after experimental radical alveolectomy, mandibular ridge augmentation by injection of HA/PP into a subperiosteal tunnel was much more effective than injection of HA in saline to gain adequate ridge height and support for dentures. The results indicate that this technique using HA/PP could be used to obviate additional surgery for harvesting autologous bone such as ribs or ileum for ridge augmentation and the accompanying morbidity. It may also be used as a substitute for bone grafts for massive bone loss as a result of trauma, tumor or resorption and for orthopedic surgical reconstruction.

The PATS reaction provides for an excellent stain to evaluate fibrovascular tissue. The clarity and contrast provided by the PATS stain reaction is excellent for observing reticular fibers and collagenous tissue.

TABLE 1

| | INCORPORATION OF IMPLANT PARTICLES INTO BONE | | | | |
|---|---|---|---|---|---|
| Implant Material | Time of Sacrifice | % Defects Completely Filled | Number of Implants | Number of Defects Showing Particle Ossification | % Defects Showing Particle Ossification |
| Calcitite/BSA | 16 wks | 100 | 4 | 0 | 0 |
| Calcitite/Collagen | 16 wks | 100 | 1 | 0 | 0 |
| Calcitite/Plaster | 16 wks | 100 | 3 | 1 | 33 |
| | 3 wks | 100 | 12 | 6 | 50 |
| Durapatite/Plaster | 3 wks | 100 | 12 | 1 | 8 |

While the invention has been described above in connection with bone implants, it will be appreciated that various modifications are possible taking into account the fact that PP is well tolerated by the human body, is rather rapidly resorbed and replaced by connective tissues, and elicits no immunologic or inflammatory response.

These advantageous characteristics indicate that PP may also be effectively used as a biodegradable scaffold for implant materials other than those utilized specifically for bone repair. Thus, for example, the use of PP as a scaffold for medicant implants, or implantable controlled-release drug delivery systems is contemplated (e.g. encapsulated therapeutic agents—such as silicone or plastic encapsulated agents). For example, PP may be used to contain chemotherapeutic or radiotherapeutic agents. The compatibility of PP with a wide variety of medicinal agents (as well as tissues) is well known. The rates of setting and resorption of gypsum products can vary greatly depending upon fabrication parameters, temperatures, pressures, and the presence of foreign ions, etc. However, mixing PP with nontoxic biodegradable polymers such as polylactic/glycolic acid, or polypeptides of glutamic acid and leucine, which are currently receiving intensive tests as polymer matrices for both topical and systemic controlled release of drugs, should not present any problem and, in fact, such biodegradable polymers and even n-butyl-2-cyanoacrylate could be used to alter the rate of resorption of plaster for the uses proposed herein.

Based on the results described herein, Plaster of Paris may be used in drug delivery as a scaffold in medicant implants to facilitate placement and containment of therapeutic agents in cancer therapy and surgery for major trauma. Thus, the use of PP as a bioresorbable vehicle or binder need not be limited to placement and containment of non-resorbable calcium materials such as hydroxylapatite particles for bone repair. PP can serve in a similar manner as a biodegradable component of an implant for delivering healing factors to areas of major trauma in addition to areas of bone injury.

Plaster has many unique characteristics which can be utilized for physical reapproximation of wounded or severed internal components. Indeed, we have found that PP by itself stimulates revascularization and angiogenesis when implanted into bony defects, as well as ossification. It is known that tissue repair, and indeed bone repair, cannot occur without generation of new blood vessels or neoangiogenesis. This is necessary to bring oxygen and nutrients to the repair site. Many of the factors which are important in neoangiogenesis are also important in osteogenesis. Fibrin or its derivatives, which can act as a scaffold for collagen deposition in repair processes could be locally or internally administered in a plaster appliance.

Plaster in medicant implants, as a scaffold for the local and contained delivery of chemotherapeutic and short-lived radioisotope agents to inoperable tumors, offers oncologists a new therapeutic approach. The active agents, e.g., encapsulated or microencapsulated in silicone rubber are known, could be applied locally in a more efficient manner, and with less morbidity than is current practice using PP according to the present invention. The fibrous connective tissue capsule which forms around the individual implant particles as the plaster is resorbed, not only modifies the release of the therapeutic agent but also helps to contain it.

Other modifications will also be evident to those in the art on the basis of the foregoing description. Furthermore, the invention may comprise, consist or consist essentially of the sequences and materials recited herein.

What is claimed is:

1. An animal implant comprising a scaffold material composed of Plaster of Paris and a non-bioresorbable calcium material bound within said Plaster of Paris.

2. The implant of claim 1 wherein said non-bioresorbable material is calcium ceramic particles selected from calcium phosphate, calcium triphosphate or mixtures thereof.

3. The implant of claim 1 containing an effective amount of a medicament bound within said plaster.

4. The implant of claim 1 containing a support material.

5. The implant of claim 4 wherein said support material is stainless steel.

6. The implant of claim 4 wherein said support material is metallic or plastic mesh.

7. The implant of claim 1 consisting essentially of Plaster of Paris and from about 0.5 to 6 parts by weight of calcium phosphate ceramic particles per part of plaster.

8. A composition suitable for use as a bone implant comprising calcium phosphate ceramic particles and Plaster of Paris as a binder for said particles.

9. The composition of claim 8 in an injectable, fluid form.

10. The composition of claim 8 in a preformed shape.

11. The composition of claim 8 wherein the ratio of calcium phosphate to plaster, on a weight basis, is approximately 0.5–6 parts of calcium phosphate per part of plaster.

12. A method of providing a bone implant in an animal which comprises injecting the composition of claim 8 in fluid or semisolid form into the appropriate body location of an animal.

13. A method of providing a bone implant in an animal which comprises inserting a preform of the composition of claim 8 into the appropriate location of an animal.

14. A method for replacing fibrous connective tissue in an animal which comprises implanting the implant of claim 1 in an animal about a fracture locus within said animal.

15. A method of treating an animal in need of a medicament which comprises implanting within said animal at an effective locus, the implant of claim 3.

16. A method of healing a fracture area within the body of an animal which comprises implanting at the locus of said fracture the implant of claim 1.

17. The implant of claim 7 consisting essentially of about 1 part by weight of ceramic particles per part of plaster.

18. The composition of claim 11 wherein the ratio of calcium phosphate to plaster, on a weight basis, is approximately 1 to 1.

* * * * *